US012419931B2

(12) United States Patent
Marais et al.

(10) Patent No.: US 12,419,931 B2
(45) Date of Patent: Sep. 23, 2025

(54) ANTI-CANCER COMPOSITION (71) Applicant: ACUPHARM INTERNATIONAL PROPRIETARY LIMITED, Gaborone (BW)

(72) Inventors: Johannes Francois Marais, Potchefstroom (ZA); Jacobus Johannes Van Jaarsveld, Potchefstroom (ZA); James Clive Hurwitz Laporta, Cape Town (ZA)

(73) Assignee: ACUPHARM INTERNATIONAL PROPRIETARY LIMITED, Gaborone (BW)

( * ) Notice: Subject to any disclaimer, the term of this patent is extended or adjusted under 35 U.S.C. 154(b) by 271 days.

(21) Appl. No.: 18/268,233

(22) PCT Filed: Dec. 15, 2021

(86) PCT No.: PCT/IB2021/061744
§ 371 (c)(1),
(2) Date: Jun. 18, 2023

(87) PCT Pub. No.: WO2022/130225
PCT Pub. Date: Jun. 23, 2022

(65) Prior Publication Data
US 2024/0293498 A1  Sep. 5, 2024

(30) Foreign Application Priority Data

Dec. 18, 2020 (NL) ...................................... 2027153

(51) Int. Cl.
*A61K 36/9066* (2006.01)
*A61K 36/48* (2006.01)
*A61P 35/00* (2006.01)

(52) U.S. Cl.
CPC .......... *A61K 36/9066* (2013.01); *A61K 36/48* (2013.01); *A61P 35/00* (2018.01); *A61K 2236/333* (2013.01); *A61K 2236/53* (2013.01)

(58) Field of Classification Search
None
See application file for complete search history.

(56) References Cited

PUBLICATIONS

Azuine, M.A., et al., Protective role of aqueous turmeric extract against mutagenicity of direct-acting carcinogens as well as Benzo[a]pyrene-induced genotoxicity and carcinogenicity, J. Cancer Res. Clin. Oncol., 118 (1992) pp. 447-452. (Year: 1992).*

Shakila, T., et al., Antioxidant potential of Sutherlandia frutescens and its protective effects against oxidative stress in various cell cultures, BMC Complement. & Altern. Med., 14 (2014) p. 271. (Year: 2014).*

(Continued)

*Primary Examiner* — Dominic Lazaro
(74) *Attorney, Agent, or Firm* — SALIWANCHIK, LLOYD & EISENSCHENK (57) ABSTRACT The present invention relates to a composition for use in the treatment of cancer, the composition comprising an aqueously-soluble extract of curcumin and an aqueously-soluble extract of *Sutherlandia frutescens*. The present invention further relates to the method and use of such a composition in the treatment of cancer.

30 Claims, 8 Drawing Sheets (56) References Cited

PUBLICATIONS

Azuine, M. A. et al. "Protective role of aqueous turmeric extract against mutagenicity of direct-acting carcinogens as well as Benzo[a]pyrene-induced genotoxicity and carcinogenicity." Journal of Cancer Research and Clinical Oncology 118:447-452, Jan. 1, 1992.
Tobwala, Shakila et al. "Antioxidant potential of Sutherlandia frutescens and its protective effects against oxidative stress in various cell cultures." BMC Complementary & Alternative Medicine 14(1):1-11, (Year: 2014).

\* cited by examiner

ANTI-CANCER COMPOSITION

CROSS REFERENCE TO RELATED APPLICATIONS

This application is a National Stage Application of International Application Number PCT/IB2021/061744, filed Dec. 15, 2021; which claims priority to Netherland Patent Application No. 2027153, filed Dec. 18, 2020.

FIELD OF APPLICATION OF THE INVENTION

The present invention relates to a composition for use in the treatment of cancer comprising a mixture of extracts of curcumin and *Sutherlandia frutescens*. The invention further relates to the use thereof in the manufacture of a medicament.

BACKGROUND TO THE INVENTION

Curcumin (diferuloylmethane), an orange yellow component of turmeric or curry powder, is a polyphenol natural product isolated from the rhizome of *Curcuma longa*. For centuries, curcumin has been used in medicinal preparations and as a food colorant. More recently, in vitro and in vivo studies have suggested that curcumin possesses activity against cancer, viral infection, arthritis, amyloid aggregation, oxidation and inflammation.

Curcumin is known to exert anticancer effects primarily by activating apoptotic pathways in cancer cells and inhibiting pro cancer processes, including inflammation, angiogenesis and metastasis. Curcumin targets numerous signalling pathways associated with cancer therapy, including pathways mediated by p53, Ras, phosphatidylinositol 3 kinase, protein kinase B, Wnt β catenin and the mammalian target of rapamycin. Clinical studies have further demonstrated that curcumin alone or combined with other drugs exhibits promising anticancer activity in patients with breast cancer without adverse effects.

Curcumin is also known to be used as a remedy for the treatment and prevention of inflammatory diseases. Acute and chronic inflammation is a major factor in the progression of obesity, type II diabetes, arthritis, pancreatitis, cardiovascular, neurodegenerative and metabolic diseases, as well as certain types of cancer.

Here it should be noted that turmeric has a long history of use in Ayurvedic medicine for the treatment of inflammatory disorders. Recent studies on the efficacy and therapeutic applicability of turmeric have suggested that the active ingredient of tumeric is curcumin. Further studies have demonstrated that curcumin has the ability to inhibit inflammatory cell proliferation, invasion, and angiogenesis through multiple molecular targets and mechanisms of action. Curcumin is safe, non-toxic, and mediates its anti-inflammatory effects through the down-regulation of inflammatory transcription factors, cytokines, redox status, protein kinases, and enzymes that all promote inflammation. In addition, curcumin induces apoptosis through mitochondrial and receptor-mediated pathways, as well as activation of caspase cascades.

The principle disadvantage of curcumin as a medicinal compound is its low solubility when conventionally extracted. This limits its potential use in treatments such as anti-cancer medicaments, which are typically provided to the patient via intravenous (IV) injection. It is further known that the poor solubility and wettability of curcumin leads to poor dissolution and bioavailability when taken orally. Further known disadvantages of known curcumin extracts include, chemical instability, photodegradation, rapid metabolism, and short half-life.

It is further known that intravenous toxicity may occur where correct extraction and solubilization procedure is not used, with at least one known fatality due to curcumin injection provided by a naturopath. Further adverse effects are known where curcumin emulsions are used.

A lot of different formulae for curcumin extracts are presently known to be available on the market. For instance, Burgh Apotheke is presently known to offer a product marketed as "Cur-Q-Ven". Said product contains a combination of curcumin, water, ethanol, Solutol HS15 and citric acid.

*Sutherlandia frutescens* ("*Sutherlandia*") is an indigenous medicinal plant extensively used in South Africa to treat a variety of health conditions. It is a fairly widespread, drought-resistant plant that grows in the Western, Eastern, and Northern Cape provinces, some areas of KwaZulu-Natal and Botswana, varying in its chemical and genetic makeup across these geographic areas. *Sutherlandia* extracts are known to induce apoptosis in cultured carcinoma cells in in vitro studies. *Sutherlandia* extract treatment is further known to induce apoptosis and modulate the PI3-kinase pathway in colon cancer cells in vitro. A number of different preparations of *Sutherlandia* are known to be made with water or alcohol. However, their application in the treatment of cancer is limited and the specific compounds and isolates that may be of value in cancer treatment are as yet unknown.

OBJECT OF THE INVENTION

It is accordingly an object of the present invention to provide a composition for the treatment of cancer making use of extracts of *Sutherlandia* and curcumin, or derivatives and isolates thereof, which at least partially ameliorates or overcomes the disadvantages of the prior art.

SUMMARY OF THE INVENTION

According to a first aspect of the invention, there is provided a composition for use in the treatment of cancer, the composition including:
an aqueously-soluble extract of curcumin;
an aqueously-soluble extract of *Sutherlandia frutescens* ("*Sutherlandia*"); and
an aqueous carrier solution.

In terms of the present invention, 'cancer' may include, but is not limited to, myeloma, amyloidosis, solitary plasmacytoma, anaplastic large cell lymphoma, Burkitt's lymphoma, Cutaneous T-Cell Lymphoma, diffuse large B-Cell lymphoma, follicular lymphoma, lymphoblastic lymphoma, MALT lymphoma, mantle cell lymphoma, primary mediastinal large B-Cell lymphoma, nodal marginal zone B-Cell lymphoma, small lymphocytic lymphoma, thyroid lymphoma, Waldenstrom's macroglobulinaemia, hairy cell leukaemia, essential thrombocythaemia, myelofibrosis, polycythemia vera, Monoclonal Gammopathy of Unknown Significance (MGUS), myleodysplatic syndromes, chondrosarcoma, ewing's sarcoma, malignant fibrous histiocytoma of bone or osteosarcoma, osteosarcoma, rhabdomyosarcoma, heart cancer, astrocytoma, brainstem glioma, pilocytic astrocytoma, ependymoma, primitive neuroectodermal tumour, cerebellar astrocytoma, cerebral astrocytoma, glioma, medulloblastoma, neuroblastoma, oligodendroglioma, pineal astrocytoma, pituitary adenoma, visual pathway and hypothalamic glioma, breast cancer, invasive lobular carcinoma, tubular carcinoma, invasive cribriform carcinoma, medullary carcinoma, male breast cancer, phyllodes tumour, inflammatory breast cancer, adrenocortical carcinoma, islet cell carcinoma, multiple endocrine neoplasia syndrome, parathyroid cancer, pheochromocytoma, thyroid cancer, merkel cell carcinoma, uveal melanoma, retinoblastoma, anal cancer, appendix cancer, cholangiocarcinoma, carcinoid tumour, colon cancer, extrahepatic bile duct cancer, gallbladder cancer, gastric (stomach) cancer, gastrointestinal carcinoid tumour, gastrointestinal stromal tumour, hepatocellular cancer, islet cell pancreatic cancer, rectal cancer, bladder cancer, cervical cancer, endometrial cancer, extragonadal germ cell tumour, ovarian cancer, ovarian epithelial cancer, ovarian germ cell tumour, penile cancer, renal cell carcinoma, transitional cell cancer (renal pelvis and ureter), prostate cancer, testicular cancer, gestational trophoblastic tumour, transitional cell cancer (ureter and renal pelvis), urethral cancer, uterine sarcoma, vaginal cancer, vulvar cancer, wilms tumour, esophageal cancer, nasopharyngeal carcinoma, oral cancer, oropharyngeal cancer, paranasal sinus and nasal cavity cancer, pharyngeal cancer, salivary gland cancer, hypopharyngeal cancer, acute biphenotypic leukaemia, acute eosinophilic leukaemia, acute lymphoblastic leukaemia, acute myeloid leukaemia, acute myeloid dendritic cell leukaemia, AIDS-related lymphoma, anaplastic large cell lymphoma, angioimmunoblastic T-cell lymphoma, B-cell prolymphocytic leukaemia, chronic lymphocytic leukaemia, chronic myelogenous leukaemia, cutaneous T-cell lymphoma, diffuse large B-cell lymphoma, follicular lymphoma, hairy cell leukaemia, hepatosplenic T-cell lymphoma, Hodgkin's lymphoma, hairy cell leukaemia, intravascular large B-cell lymphoma, large granular lymphocytic leukaemia, lymphoplasmacytic lymphoma, lymphomatoid granulomatosis, mantle cell lymphoma, marginal zone B-cell lymphoma, mast cell leukaemia, mediastinal large B cell lymphoma, multiple myeloma/plasma cell neoplasm, myelodysplastic syndromes, mucosa-associated lymphoid tissue lymphoma, mycosis fungoides, nodal marginal zone B cell lymphoma, non-Hodgkin lymphoma, precursor B lymphoblastic leukaemia, primary central nervous system lymphoma, primary cutaneous follicular lymphoma, primary cutaneous immunocytoma, primary effusion lymphoma, plasmablastic lymphoma, Sézary syndrome, splenic marginal zone lymphoma, T-cell prolymphocytic leukaemia, basal cell carcinoma, squamous cell carcinoma, skin adnexal tumour, melanoma, Merkel cell carcinoma, sarcomas of primary cutaneous origin, lymphomas of primary cutaneous origin, bronchial adenomas, bronchial carcinoids, small cell lung cancer, mesothelioma, non-small cell lung cancer, pleuropulmonary blastoma, laryngeal cancer, thymoma and thymic carcinoma, Kaposi sarcoma, epithelioid hemangioendothelioma, desmoplastic small round cell tumour, and liposarcoma.

In an embodiment of the invention, the ratio of the aqueously-soluble extract of curcumin and the aqueously-soluble extract of *Sutherlandia* within the aqueous carrier solution may be between 2:1 and 6:1 w/v. In a preferred embodiment of the invention, the ratio may be 4:1.

In terms of the invention, the aqueously-soluble extract of curcumin may be derived from curcumin extract. Preferably, the curcumin extract may be a pre-concentrated extract comprising at least 90% curcumin by weight.

In an embodiment of the invention, the aqueously-soluble extract of curcumin and/or *Sutherlandia* may be produced by a method including:

dispersing a sample of curcumin and/or *Sutherlandia* in ethanol solution with a concentration of at least 70% w/v;
adjusting the pH of the solution to at least 10;
storing the adjusted solution for at least 24 hours;
re-adjusting the solution to a pH of 7;
storing the re-adjusted solution for at least 24 hours;
separating the supernatant from the sediment, retaining the supernatant; and
filtering the supernatant.

In an embodiment of the invention, the ratio of ethanol solution to the sample may be at least 5 ml per gram of extract. In a preferred embodiment of the invention, the ratio of ethanol solution to the sample may be 10 ml per gram of extract.

According to the invention, the solution may be adjusted to a pH of 12. The invention provides for the pH to be adjusted using sodium hydroxide.

In an embodiment of the invention, the adjusted solution may be stored for at least five days. In a preferred embodiment, the adjusted solution may be stored for ten days.

According to the invention, the re-adjusted solution may be re-adjusted using hydrochloric acid.

The re-adjusted solution may be stored for at least five days. In a preferred embodiment of the invention, the re-adjusted solution may be stored for at least ten days.

In terms of the invention, the adjusted solution may be mixed daily during storage.

The re-adjusted solution may be mixed for at most the first 50% of the storage period and then left to settle for the remaining period.

According to the invention, the *Sutherlandia* extract may be a leaf extract. It may also be a stem or root extract. According to an alternative embodiment of the first aspect of the invention, the *Sutherlandia* plant material is root material. According to another alternative embodiment of the first aspect of the invention, the *Sutherlandia* plant material is stem material.

The composition may further include a solubiliser. In a preferred embodiment of the invention, the solubiliser may be Kolliphor® HS 15 and/or Kollidon® 25.

The invention provides for the composition to be formulated for intravenous (IV) injection.

In an alternate embodiment, the composition may be formulated by drying. In a preferred alternative embodiment, the composition drying may be carried out in combination with or without a liposomal compound. In a further preferred alternative embodiment, the composition may be further formulated for oral administration using capsules or syrup.

In an embodiment of the invention, the composition may be formulated by dilution into a buffered solution.

In an alternative embodiment, the composition may be formulated for administration as a cream.

The composition may further comprise a known anti-cancer compound.

Here known anti-cancer compounds may include (but are not limited to) cyclophosphamide, mechlorethamine, chlorambucil, melphalan, dacarbazine, temozolomide, anthracyclines, daunorubicin, doxorubicin, epirubicin, idarubicin, mitoxantrone, valrubicin, paclitaxel, docetaxel, abraxane, taxotere, epothilones, vorinostat, romidepsin, irinotecan, topotecan, etoposide, teniposide, tafluposide, bortezomib, erlotinib, gefitinib, imatinib, vemurafenib, vismodegib, azacitidine, 5-fluorouracil, azathioprine, 6-mercaptopurine, capecitabine, capecitabine, cytarabine, cytarabine, doxifluridine, floxuridine, fluorouracil, fludarabine, gemcitabine, gemcitabine, hydroxyurea, hydroxycarbamide, mercaptopurine, methotrexate, methotrexate, pemetrexed, tioguanine, phototrexate, bleomycin, actinomycin, carboplatin, cisplatin, oxaliplatin, tretinoin, alitretinoin, bexarotene, vinblastine, vincristine, vindesine, vinorelbine, ado-trastuzumab emtansine, afatinib, aldesleukin, alectinib, alemtuzumab, atezolizumab, avelumab, axitinib, belimumab, belinostat, bevacizumab, blinatumomab, bortezomib, bosutinib, brentuximab vedotin, brigatinib, cabozantinib, canakinumab, carfilzomib, ceritinib, cetuximab, cobimetinib, crizotinib, dabrafenib, daratumumab, dasatinib, denosumab, dinutuximab, durvalumab, elotuzumab, enasidenib, erlotinib, everolimus, febendazole, gefitinib, ibritumomab tiuxetan, ibrutinib, idelalisib, imatinib, ipilimumab, ixazomib, lapatinib, lenvatinib, midostaurin, necitumumab, neratinib, nilotinib, niraparib, nivolumab, obinutuzumab, ofatumumab, olaparib, olaratumab, osimertinib, palbociclib, panitumumab, panobinostat, pazopanib, pembrolizumab, pertuzumab, ponatinib, ramucirumab, regorafenib, ribociclib, rituximab, rituximab/hyaluronidase human, romidepsin, rucaparib, ruxolitinib, siltuximab, sipuleucel-t, sonidegib, sorafenib, temsirolimus, tocilizumab, tofacitinib, tositumomab, trametinib, trastuzumab, vandetanib, vemurafenib, venetoclax, vismodegib, vorinostat, ziv-aflibercept, Tumor-Infiltrating Lymphocyte (TIL) therapy, Engineered T Cell Receptor (TCR) therapy, Chimeric Antigen Receptor (CAR) T cell therapy, natural killer (NK) cell therapy, axicabtagene ciloleucel, brexucabtagene autoleucel, tisagenlecleucel, indocyanin green, chlorin e6, Methylene blue, ALA, photosense, and combinations thereof.

The composition may further comprise a known natural or naturally-derived compound.

Here known natural or naturally-derived compounds may include, but are not limited to, aloe, *Artemesia absinthium, Artemesia affra, Artemesia aulgaris, Artemesinin, Artemsia annua, Artesunat, Artesunate*, ascorbic acid, berberine, *Bidens pilosa*, bioperine, boswellia, *Centella asiatica, Cnicus Benedictus, Cordyceps* spp., *Drosera capensis, Ganoderma* a spp., Genesteine, gingerol, ginseng, ginsenoside, ginsenosoides, green rooibos, honeybush broad leaf, *Hypoestes aristate, Hypoxis haemor*, indirubin, *Leonotis leonurus, Mimosa pudicca*, moringa, *Nigella Sativa*, olive leaf extract, oridonin, oxymutrine, proancocydin, quercetin, resveratrol, sutherak, tanhinone, tanshins, thin leaf honeybush, thymoquinone, ursolic acid, vitamin C, vitamin K3, xalpalthinin, SAC-Calcium and combinations thereof.

According to a second aspect thereof, there is provided a composition, substantially has herein described, for use in the treatment of cancer.

According to a third aspect thereof, there is provided a composition, substantially has herein described, for use in a method for treating cancer.

According to a fourth aspect thereof, there is provided a method of treating cancer, comprising administering the composition substantially has herein described, to a subject in need thereof.

According to a fifth aspect thereof, there is provided the use of a composition of, substantially has herein described, in the manufacture of a medicament for the treatment of cancer.

The above and other characteristics, features and advantages of the present invention will become apparent from the following detailed description, taken in conjunction with the accompanying drawing which illustrate, by way of example, the principles of the invention. This description is given for the sake of example only, without limiting the scope of the invention. The reference figures quoted below refer to the attached drawings.

BRIEF DESCRIPTION OF THE DRAWINGS

One embodiment of the invention is described below, by way of a non-limiting example only, and with reference to the accompanying drawings in which.

The presently disclosed subject matter will now be described more fully hereinafter with reference to the accompanying Example, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

DESCRIPTION OF PREFERRED EMBODIMENTS OF THE INVENTION

A non-limiting example of a preferred embodiment of the invention is described in more detail below, with reference to the Figures.

Example 1

Curcumin Extraction and Processing

In order to obtain an aqueously-soluble curcumin extract 100 g of a commercially-available 95% Curcumin powder extract combined with 500 ml of 90% ethanol diluted from absolute alcohol using deionised water. This solution was then stirred or shaken until all the powder was dispersed in the solution. In a separate container a 25% Sodium Hydroxide solution was then prepared, which was used to adjust the pH of the solution of between 10 and 12. After adjustment the solution was then stored at room temperature for 10 days, being mixed every day. Following storage, the solution was re-adjusted to a pH of between 6 and 7 using HCl and stored for another ten days at room temperature. The re-adjusted solution was mixed daily for the first five days, then left to settle. Thereafter the solution was separated from the sediment and filtered, before being sent for HPLC analysis to determine the concentration of Curcumin in mg/ml.

Here the use of mixture and settling rather than sonication and filtration appears to be important in obtaining the favourable results seen in vitro.

Sutherlandia Extraction and Processing

In order to make an extract of Sutherlandia a 100 g sample of Sutherlandia plant matter, in the form of either leaf, stem or root matter, is processed using the same method as described herein above for curcumin.

After extraction, the curcumin and Sutherlandia extracts were formulated in a ratio of 4:1 w/v. These were then combined with solubilisers in the form of Kolliphor® HS 15. The combination of curcumin and Sutherlandia extracts is intended for use as a medicament to treat many cancer subtypes in combination chemotherapies or targeted chemotherapies.

Example 2

Comparative studies were performed using curcumin extract as described above (referred to as ACPJL 08), Sutherlandia leaf extract in water (referred to as ACPJL 35), Sutherlandia leaf extract in 50% ethanol and water solution (referred to as ACPJL 28), Sutherlandia leaf extract in 90% ethanol and water solution (referred to as ACPJL 07) and a combinatorial formulation using the curcumin extract and Sutherlandia leaf extract in water and alcohol according to this invention (referred to as ACPJL 20). These extracts were compared to a number of known botanical isolates with anti-cancer activity, as well as a number of known anti-cancer drugs, using a dose response design with cumulative cell death as the dependent variable. These studies were conducted on in vitro samples of cultured tissue, taken as biopsy samples from patients as part of a standard culture and testing process done in order to optimise treatment.

A representative sample of such a study is provided herein below.

Summary of Study of Patient with Assigned Number 19055

Figure 1:
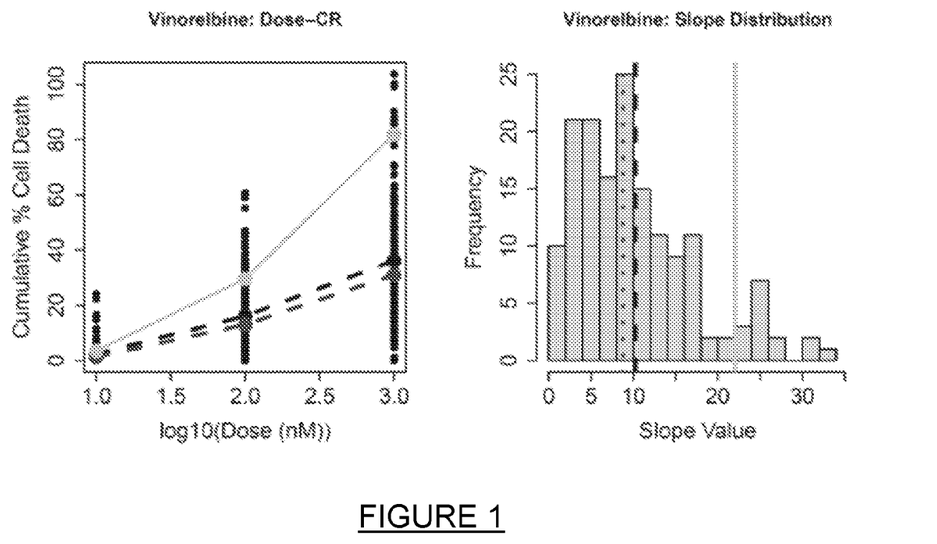
FIG. 1 depicts a graph illustrating a control sample Vinorelbine.
Figure 2:
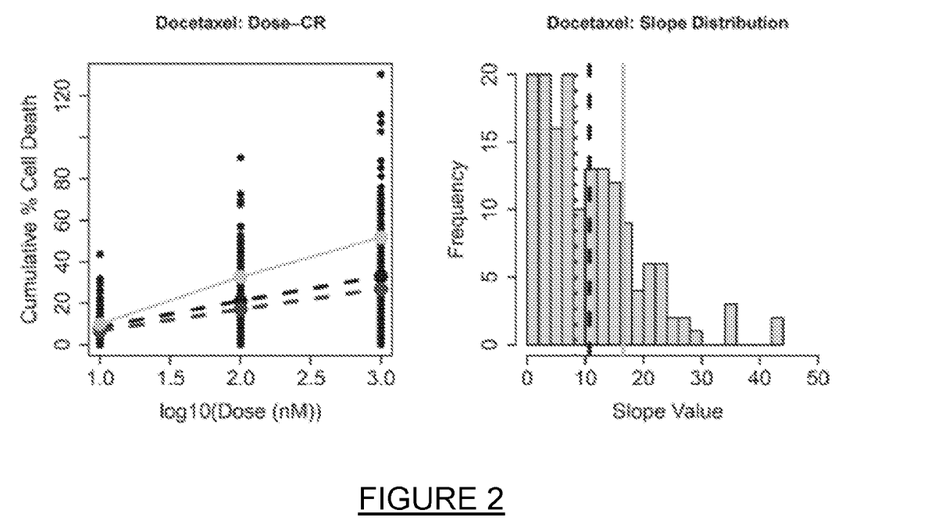
FIG. 2 depicts a graph illustrating a control sample Docetaxel.
Figure 3:
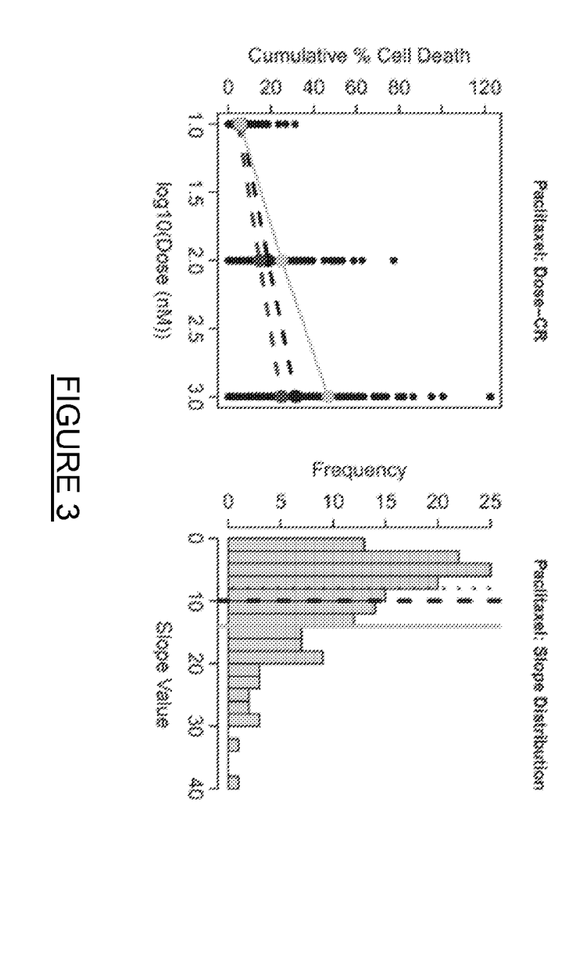
FIG. 3 depicts a graph illustrating a control sample Paclitaxel.
Figure 4:
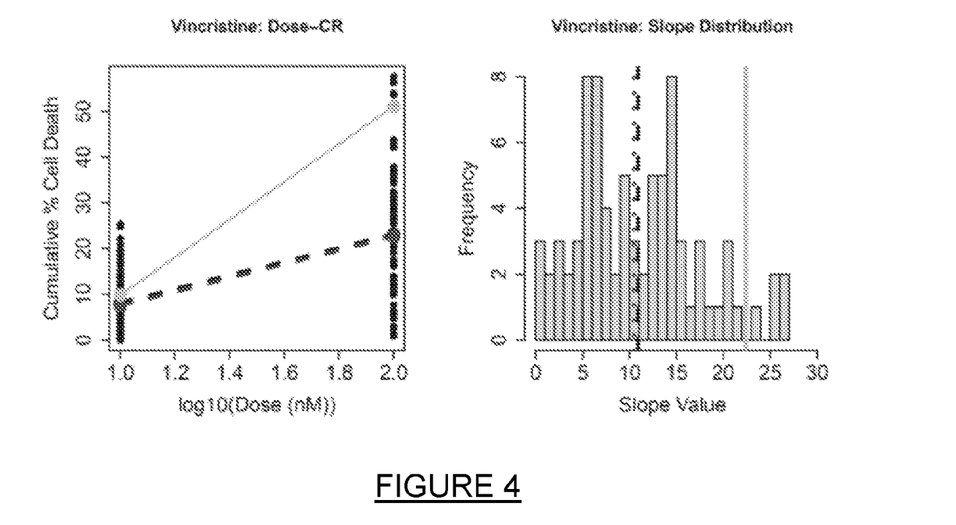
FIG. 4 depicts a graph illustrating a control sample Vincristine.
Figure 5:
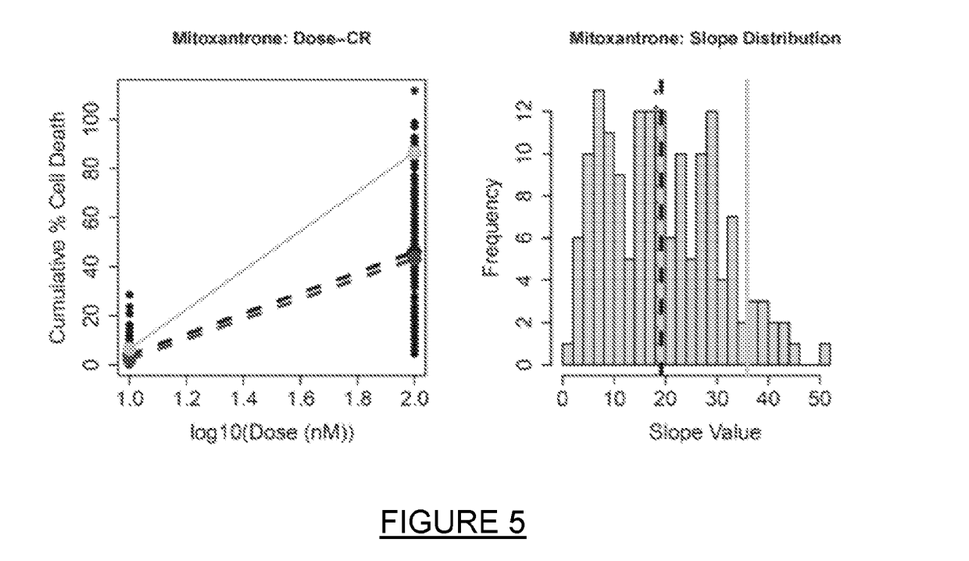
FIG. 5 depicts a graph illustrating a control sample Mitoxantrone.
Figure 6:
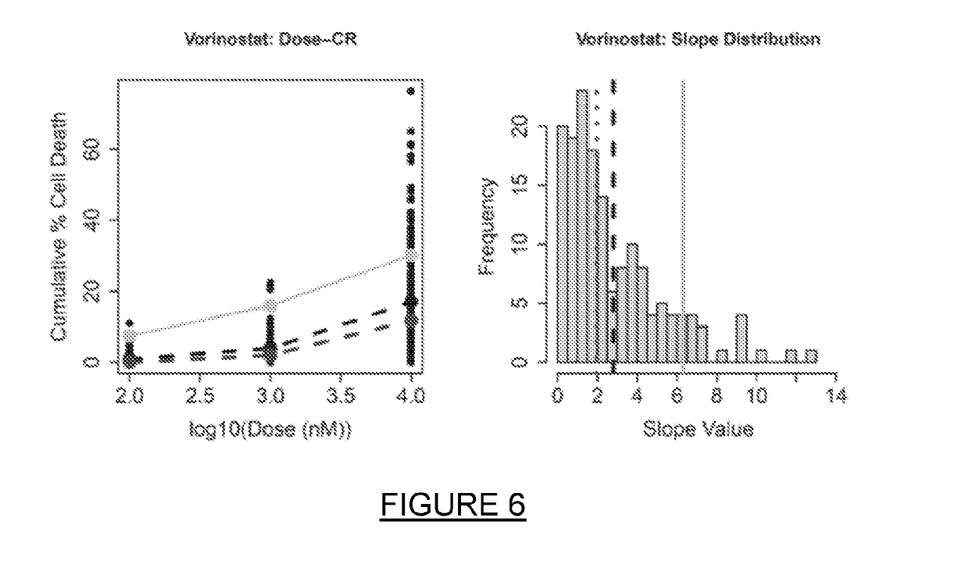
FIG. 6 depicts a graph illustrating a control sample Vorinostat.
Figure 7:
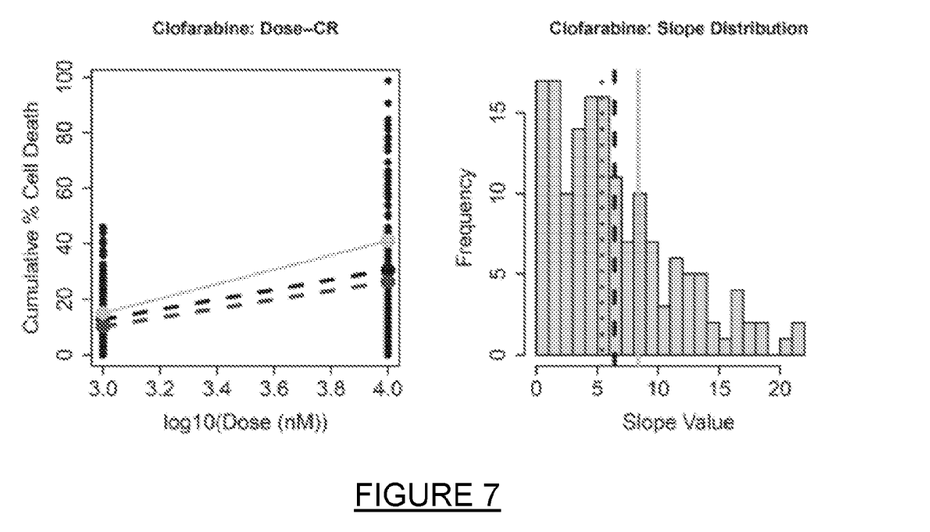
FIG. 7 depicts a graph illustrating a control sample Clofarabine.
Figure 8:
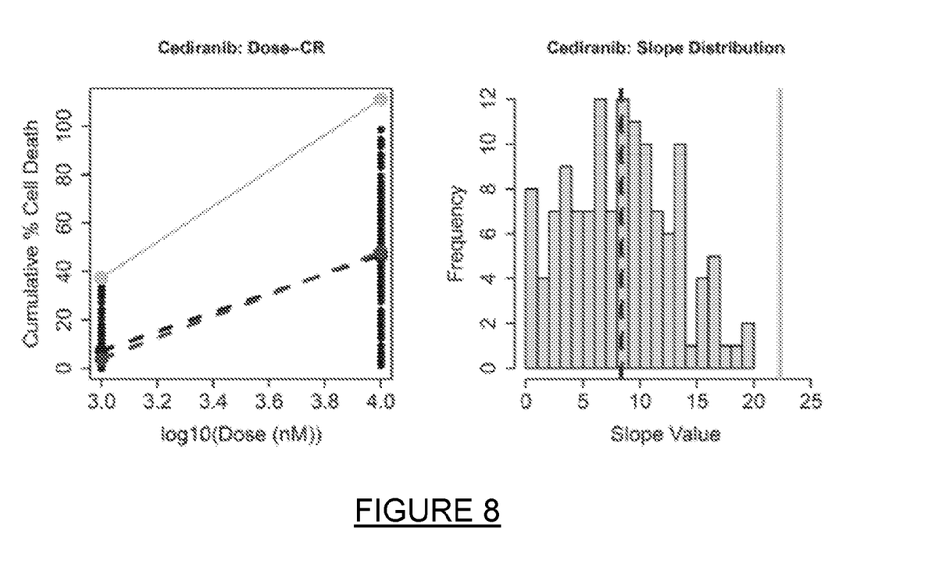
FIG. 8 depicts a graph illustrating a control sample Cediranib.
Figure 9:
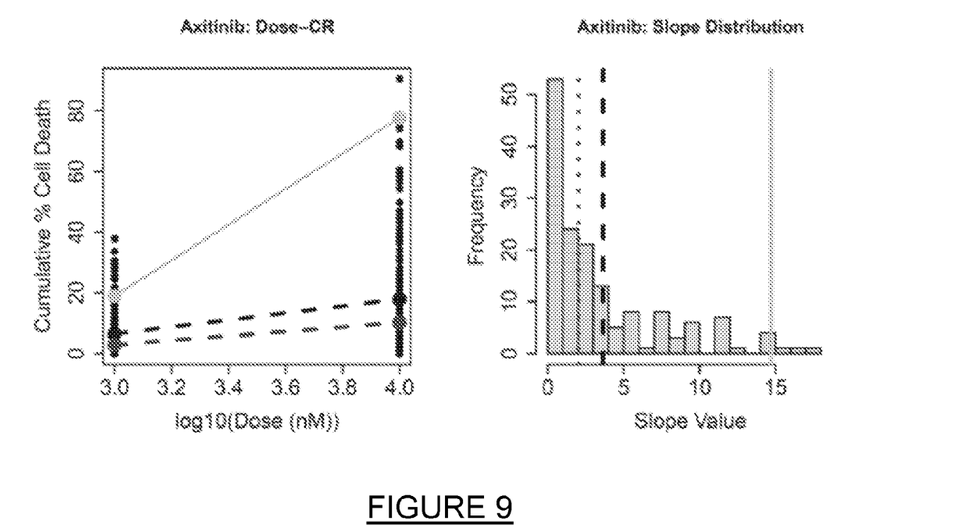
FIG. 9 depicts a graph illustrating a control sample Axitinib.
Figure 10:
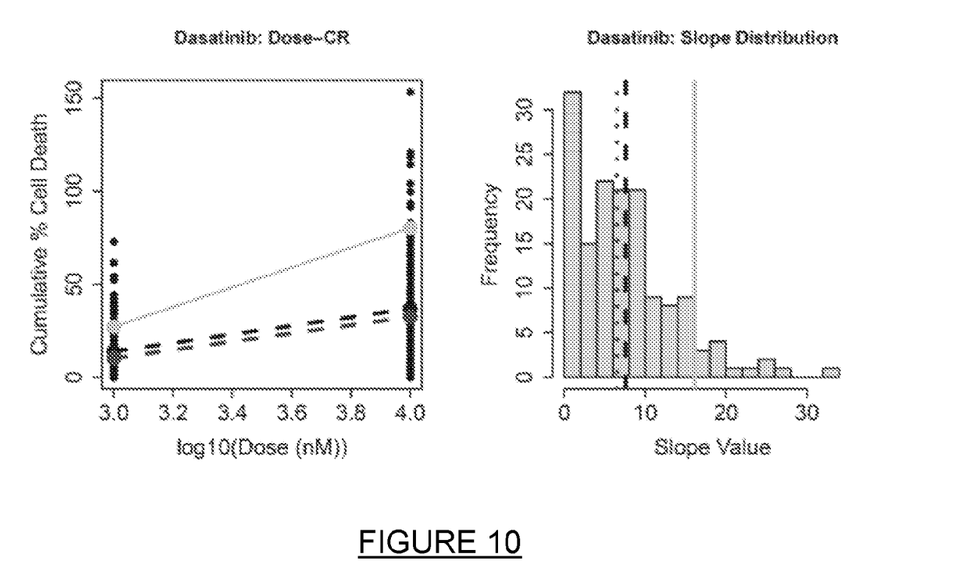
FIG. 10 depicts a graph illustrating a control sample Dasatinib.
Figure 11:
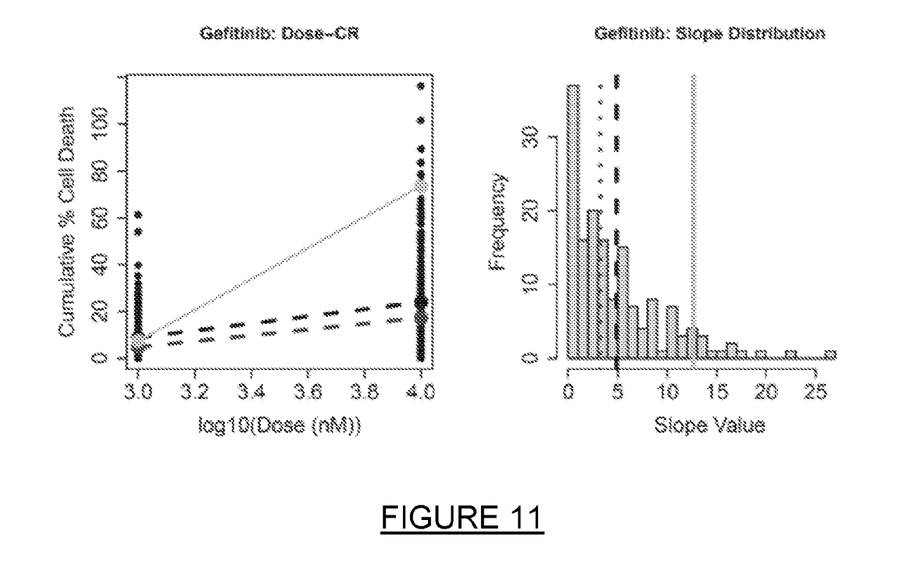
FIG. 11 depicts a graph illustrating a control sample Gefitinib.
Figure 12:
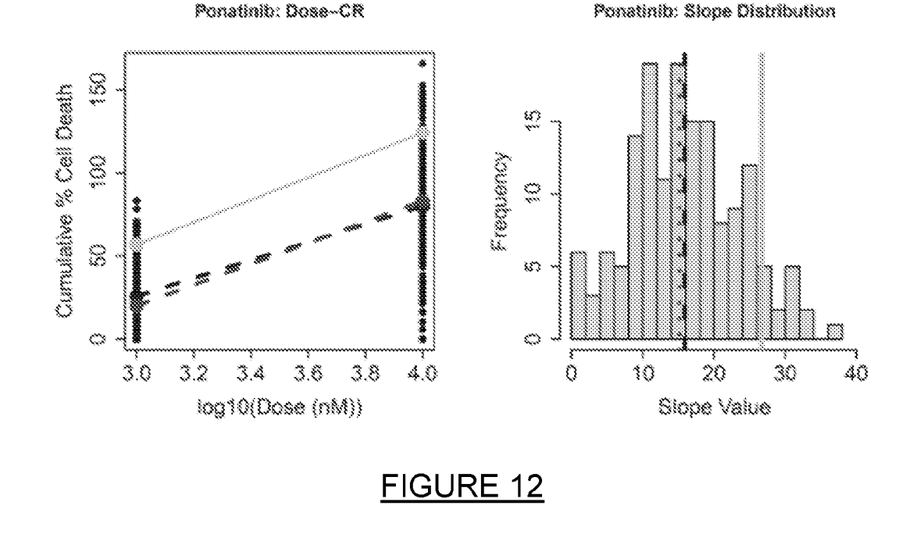
FIG. 12 depicts a graph illustrating a control sample Ponatinib.
Figure 13:
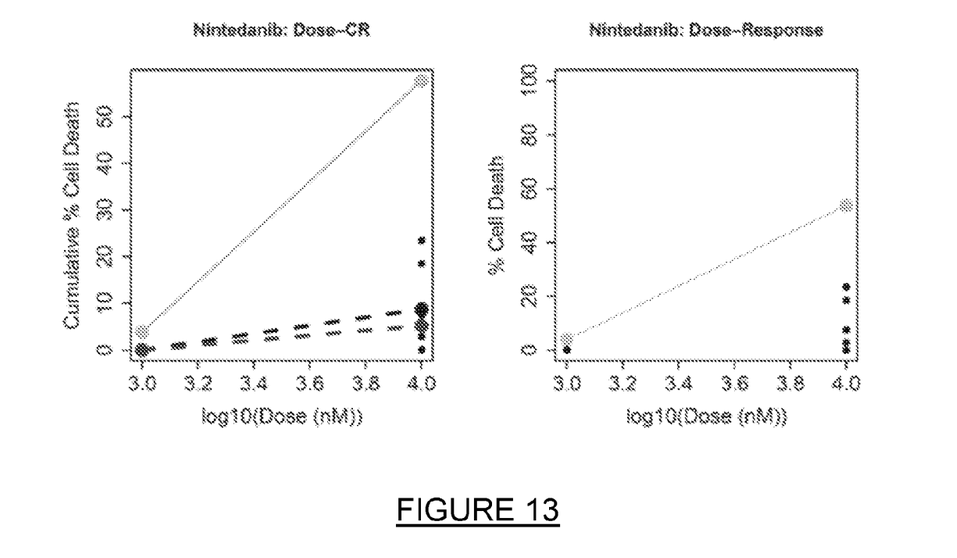
FIG. 13 depicts a graph illustrating a control sample Nintedanib.

Patient from whom sample was obtained was a 70-year-old female presenting with a diagnosis of Breast DCIS papillary neoplasm. The sample was obtained via needle biopsy, before being cultured. As part of the standard testing process a number of non-targeted drugs (Vinorelbine, Docetaxel, Paclitaxel, Vincristine, Mitoxantrone, Vorinostat, Clofarabine, the dose-CR curves and slope distributions for which can be seen in FIGS. 1 to 7 and targeted drugs (Cediranib, Axitinib, Dasatinib, Gefitinib, Ponatinib, the dose-CR curves and slope distributions for which can be seen in FIGS. 8 to 12) were identified as having potential benefit. Another drug, Nintedanib, was identified as a new drug having good efficacy and a positive dose response curve (as seen in FIG. 13).

Figure 14:
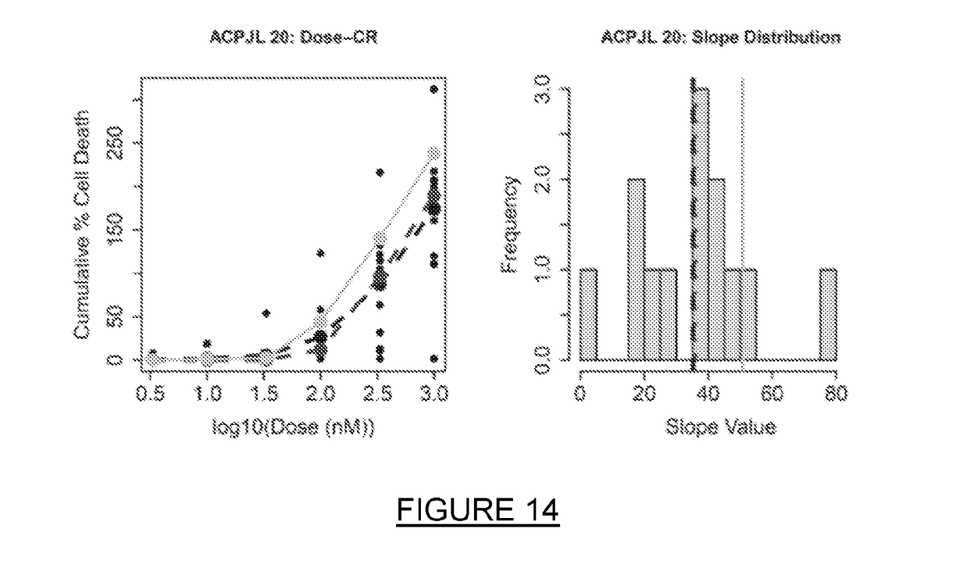
FIG. 14 depicts a graph illustrating the present invention labelled ACPJL 20.
Figure 15:
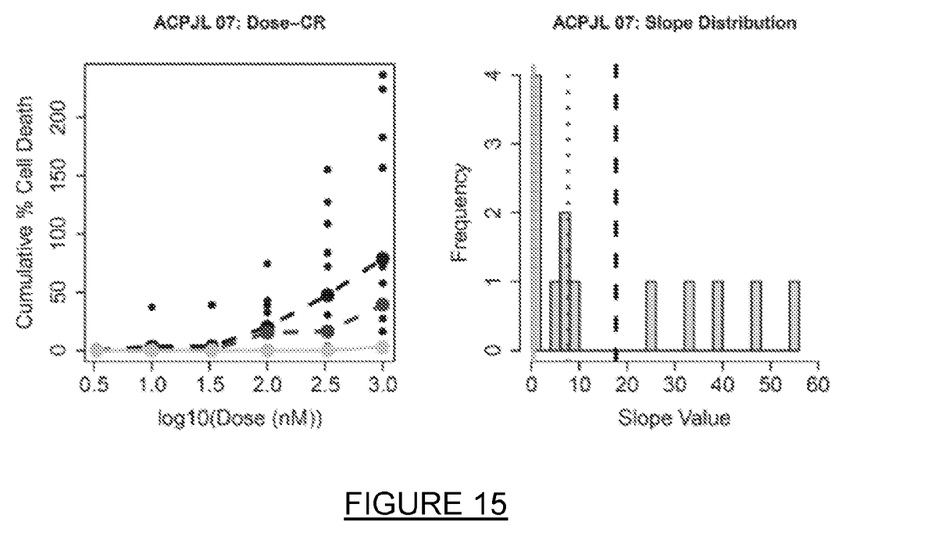
FIG. 15 depicts a graph illustrating the present invention labelled ACPJL 07.
Figure 16:
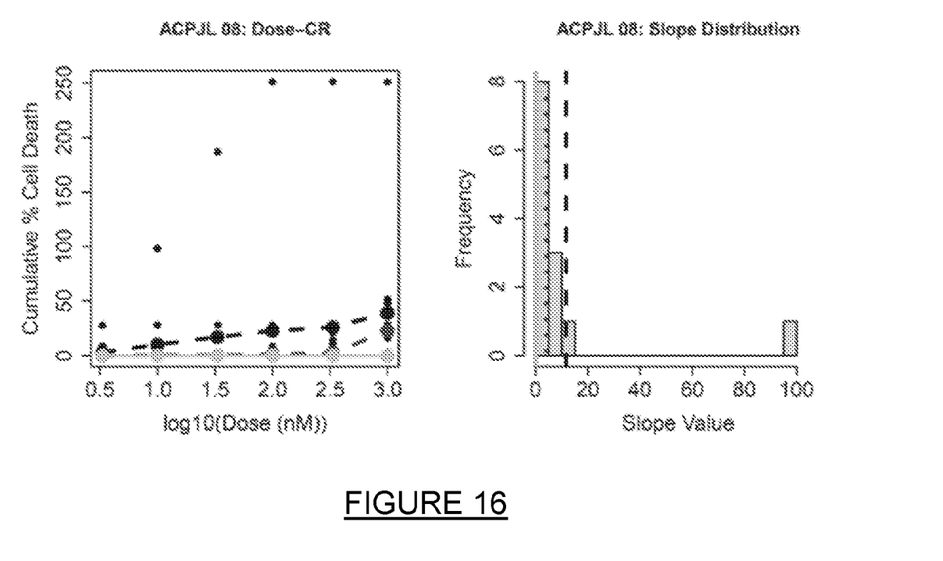
FIG. 16 depicts a graph illustrating the present invention labelled ACPJL 08.

Of the botanicals tested, ACPJL 20 (the dose-CR curve and slope distribution for which can be seen in FIG. 14) was identified as having potential benefit. Of interest here is the comparison of ACPJL 07 (the dose-CR curve and slope distribution for which can be seen in FIG. 15), ACPJL 08 (the dose-CR curve and slope distribution for which can be seen in FIG. 16) and ACPJL 20, which is a combination of the two. Here an unexpected synergistic effect is evident, with both of the constituents demonstrating low patient dose-CR and slope values. In contrast, the cumulative percentage cell death seen for ACPJL 20 rises steeply from the 2 log 10 (Dose (nM)) point, while the patient-derived slope value is around 50. This synergistic effect is seen in a number of samples tested, and demonstrates the potential usefulness of the novel, combinatorial composition comprised of the curcumin and Sutherlandia extracts obtained by the methods described herein above.

The invention claimed is:

1. A composition for use in the treatment of cancer, the composition including:
    an aqueously-soluble extract of curcumin;
    an aqueously-soluble extract of Sutherlandia frutescens ("Sutherlandia"); and
    an aqueous carrier solution.

2. The composition of claim 1, wherein a ratio of the aqueously-soluble extract of curcumin to the aqueously-soluble extract of Sutherlandia within the aqueous carrier solution is between 2:1 and 6:1 w/v.

3. The composition of claim 2, wherein the ratio is 4:1.

4. The composition of claim 1, wherein the aqueously-soluble extract of curcumin is derived from curcumin extract.

5. The composition of claim 2, wherein the curcumin extract is a pre-concentrated extract comprising at least 90% curcumin by weight.

6. The composition of claim 1, wherein the aqueously-soluble extract of curcumin and/or Sutherlandia is produced by a method comprising:
    dispersing a sample of curcumin or Sutherlandia in ethanol solution with a concentration of at least 70% w/V;
    adjusting the pH of the solution to at least 10;
    storing the adjusted solution for at least 24 hours;
    re-adjusting the solution to a pH of 7;
    storing the re-adjusted solution for at least 24 hours;
    separating the supernatant from the sediment, retaining the supernatant; and
    filtering the supernatant.

7. The composition of claim 6, wherein the ratio of ethanol solution to the sample is at least 5 ml per gram of extract.

8. The composition of claim 7, wherein the ratio of ethanol solution to the sample is 10 ml per gram of extract.

9. The composition of claim 6, wherein the solution is adjusted to a pH of 12.

10. The composition of claim 6, wherein the pH is adjusted using sodium hydroxide.

11. The composition of claim 6, wherein the adjusted solution is stored for at least five days.

12. The composition of claim 7, wherein the adjusted solution is stored for ten days.

13. The composition of claim 6, wherein the re-adjusted solution is re-adjusted using hydrochloric acid.

14. The composition of claim 6, wherein the re-adjusted solution is stored for at least five days.

15. The composition of claim 14, wherein the re-adjusted solution is stored for at least ten days.

16. The composition of claim 6, wherein the adjusted solution is mixed daily during storage.

17. The composition of claim 6, wherein the re-adjusted solution is mixed for at most the first 50% of the storage period and then left to settle for the remaining period.

18. The composition of claim 1, wherein the Sutherlandia extract is a leaf extract.

19. The composition of claim 1, wherein the composition further includes a solubiliser.

20. The composition of claim 19, wherein the solubiliser is Kolliphor® HS 15 and/or Kollidon® 25.

21. The composition of claim 1 wherein the composition is formulated for intravenous (IV) injection.

22. The composition of claim 1, wherein the composition is formulated by drying.

23. The composition of claim 22, wherein the composition drying is carried out in combination with a liposomal compound.

24. The composition of claim 22, wherein the composition is further formulated for oral administration using capsules.

25. The composition of claim 1, wherein the composition is formulated by dilution into a buffered solution.

26. The composition of claim 1, wherein the composition is formulated for administration as a cream.

27. The composition of claim 1, wherein the composition further comprises a known anti-cancer compound.

28. The composition of claim 1, wherein the composition further comprises a known natural or naturally-derived compound.

29. A method of treating cancer, comprising administering the composition of claim 1 to a subject in need thereof.

30. The composition of claim 1 for use in the manufacture of a medicament for the treatment of cancer.

\* \* \* \* \*